(12) United States Patent
Yadlowsky et al.

(10) Patent No.: US 9,028,400 B2
(45) Date of Patent: May 12, 2015

(54) COUNTER-ROTATING OPHTHALMIC SCANNER DRIVE MECHANISM

(75) Inventors: Michael J. Yadlowsky, Sunnyvale, CA (US); Michael James Papac, North Tustin, CA (US); John Christopher Huculak, Mission Viejo, CA (US)

(73) Assignee: Novartis AG, Basel (CH)

( * ) Notice: Subject to any disclaimer, the term of this patent is extended or adjusted under 35 U.S.C. 154(b) by 163 days.

(21) Appl. No.: 13/354,429

(22) Filed: Jan. 20, 2012

(65) Prior Publication Data

US 2012/0190921 A1    Jul. 26, 2012

Related U.S. Application Data

(60) Provisional application No. 61/434,942, filed on Jan. 21, 2011.

(51) Int. Cl.
| | |
|---|---|
| *A61B 1/06* | (2006.01) |
| *G02B 26/08* | (2006.01) |
| *G02B 26/10* | (2006.01) |
| *G02B 26/12* | (2006.01) |

(Continued)

(52) U.S. Cl.
CPC ............ *A61B 5/0066* (2013.01); *A61B 1/00172* (2013.01); *A61B 3/102* (2013.01); *A61B 5/0084* (2013.01); *A61B 5/6848* (2013.01); *A61B 2562/0233* (2013.01); *A61F 9/007* (2013.01); *G01N 21/4795* (2013.01)

(58) Field of Classification Search
CPC ... A61B 5/0066; A61B 3/102; A61B 1/00172

USPC ........ 351/206; 359/203.1; 600/103, 128–129, 600/137, 160, 171, 173, 175–176
See application file for complete search history.

(56) References Cited

U.S. PATENT DOCUMENTS

| | | | |
|---|---|---|---|
| 5,595,565 A | 1/1997 | Treat et al. | |
| 6,004,314 A | 12/1999 | Wei et al. | |

(Continued)

FOREIGN PATENT DOCUMENTS

| | | |
|---|---|---|
| DE | 10 2008 036420 | 11/2010 |
| GB | 2222953 | 11/2010 |

(Continued)

OTHER PUBLICATIONS

Han et al., "Handheld forward-imaging needle endoscope for ophthalmic optical coherence tomography inspection", Journal of Biomedical Optics, Mar./Apr. 2008, vol. 13(2), pp. 020505-1 thru 020505-3.

(Continued)

*Primary Examiner* — John P Leubecker
*Assistant Examiner* — Ronald D Colque

(57) ABSTRACT

An endoprobe for ophthalmic microsurgical procedures including a hand-piece including a motor, a cannula assembly coupled to the hand-piece, and a transmission system coupling the motor to the cannula assembly is provided. The cannula assembly having an outer tube and an inner tube concentric with the outer tube, each able to rotate about the longitudinal axis and having a proximal end and a distal end. The transmission system rotates the outer tube in a first direction and the inner tube in a second, opposing direction about the longitudinal axis. A method for scanning a light beam along a linear trajectory using a cannula assembly as above is also provided.

17 Claims, 5 Drawing Sheets

(51) Int. Cl.
  *A61B 5/00*    (2006.01)
  *A61B 1/00*    (2006.01)
  *A61B 3/10*    (2006.01)
  *A61F 9/007*   (2006.01)
  *G01N 21/47*   (2006.01)

(56) References Cited

U.S. PATENT DOCUMENTS

| | | | |
|---|---|---|---|
| 6,485,413 | B1 | 11/2002 | Boppart et al. |
| 7,261,687 | B2 | 8/2007 | Yang |
| 7,364,543 | B2 | 4/2008 | Yang et al. |
| 7,602,540 | B2 | 10/2009 | Masuda et al. |
| 8,325,988 | B2 | 12/2012 | Ren et al. |
| 2005/0020926 | A1 | 1/2005 | Wiklof et al. |
| 2005/0234345 | A1* | 10/2005 | Yang .............................. 600/476 |
| 2006/0004397 | A1 | 1/2006 | Osawa |
| 2007/0066871 | A1* | 3/2007 | Yang et al. .................... 600/173 |
| 2007/0265602 | A1 | 11/2007 | Mordaunt et al. |
| 2008/0051770 | A1 | 2/2008 | Scheller et al. |
| 2008/0228404 | A1 | 9/2008 | Garty et al. |
| 2009/0198125 | A1 | 8/2009 | Nakabayashi et al. |
| 2010/0228132 | A1* | 9/2010 | Brennan et al. ............... 600/478 |
| 2010/0228238 | A1* | 9/2010 | Brennan et al. ................. 606/13 |
| 2011/0184390 | A1 | 7/2011 | Zanni et al. |
| 2011/0279821 | A1 | 11/2011 | Brennan et al. |
| 2011/0282190 | A1 | 11/2011 | Caffey et al. |
| 2011/0282191 | A1 | 11/2011 | Brennan et al. |
| 2011/0282331 | A1 | 11/2011 | Brennan et al. |
| 2012/0075639 | A1 | 3/2012 | Brennan et al. |
| 2013/0038836 | A1 | 2/2013 | Smith |
| 2013/0267776 | A1* | 10/2013 | Brennan et al. ............... 600/109 |

FOREIGN PATENT DOCUMENTS

| | | |
|---|---|---|
| WO | 2007/038682 | 4/2007 |
| WO | 2008/079526 | 7/2008 |

OTHER PUBLICATIONS

Wu et al., "Paired-angle-rotation scanning optical coherence tomography forward-imaging probe", Optics Letters, May 2006, vol. 31(9), 1265-1267.

Yaqoob et al., "Methods and application areas of endoscopic optical coherence tomography", Journal of Biomedical Optics, Nov./Dec. 2006, vol. 11(6), pp. 063001-1 thru 063001-19.

PCT International Search Report for corresponding PCT/US2012/021969 with mailing date Jul. 9, 2012, 5 pages.

Tearney GJ et al., "Scanning single-mode fiber optic catheter-endoscope for optical coherence tomography", Optics Letters, Apr. 1, 1996, vol. 21(7), pp. 543-545.

* cited by examiner

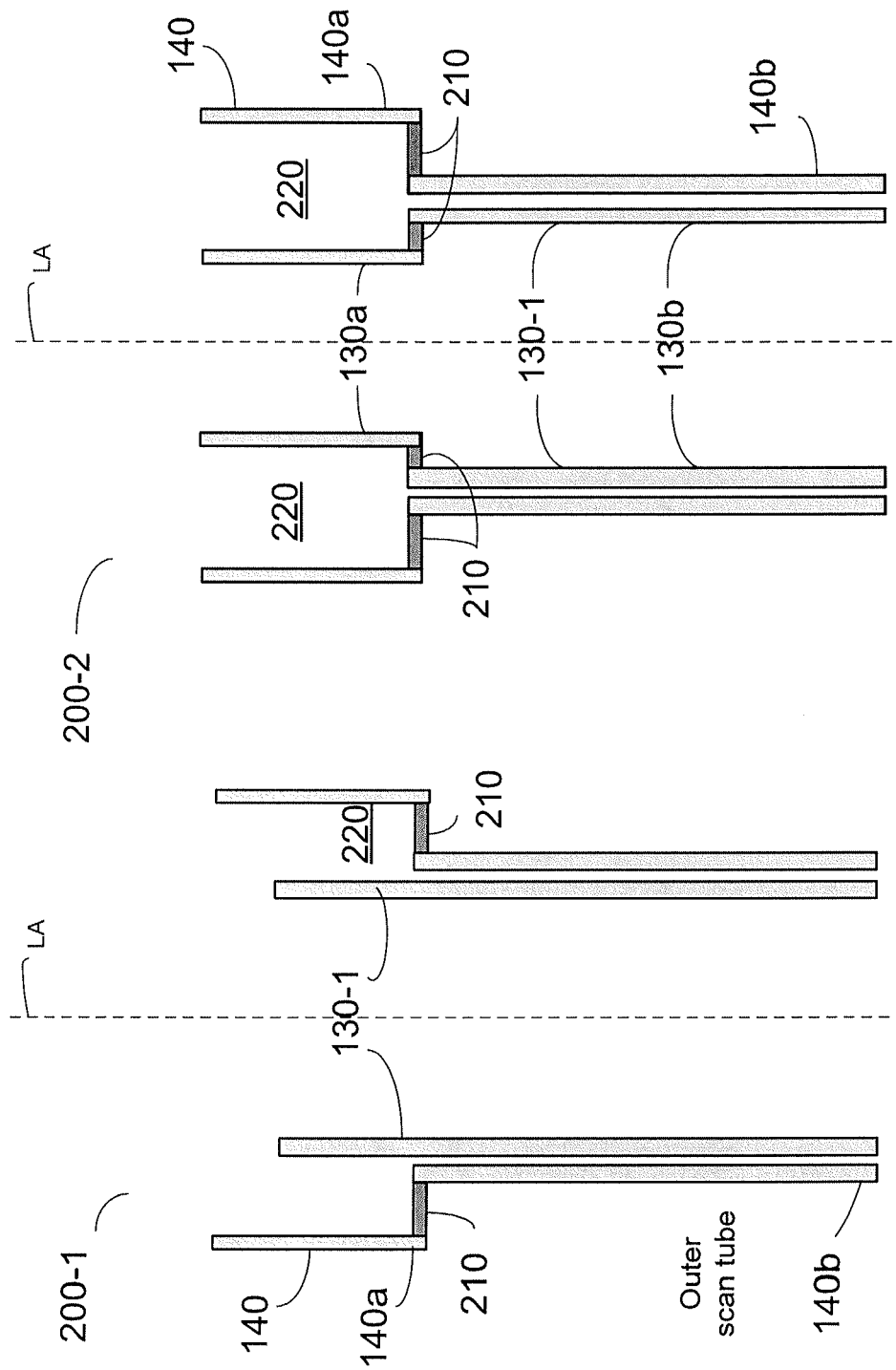

COUNTER-ROTATING OPHTHALMIC SCANNER DRIVE MECHANISM

CROSS-REFERENCE TO RELATED APPLICATION

The present application claims priority based on U.S. Provisional Patent Application Ser. No. 61/434,942 filed Jan. 21, 2011.

BACKGROUND

1. Field of the Invention

Embodiments described herein relate to the field of microsurgical probes. More particularly, embodiments described herein are related to the field of endoscopic Optical Coherence Tomography (OCT) and to the field of ophthalmic microsurgical techniques.

2. Description of Related Art

The field of microsurgical procedures is evolving rapidly. Typically, these procedures involve the use of probes that are capable of reaching the tissue that is being treated or diagnosed. Such procedures make use of endoscopic surgical instruments having a probe coupled to a controller device in a remote console. Current state of the art probes are quite complex in operation, often times requiring moving parts that are operated using complex mechanical systems. In many cases, an electrical motor is included in the design of the probe. Most of the prior art devices have a cost that makes them difficult to discard after one or only a few surgical procedures. Furthermore, the complexity of prior art devices leads generally to probes having cross sections of several millimeters. These probes are of little practical use for ophthalmic microsurgical techniques. In ophthalmic surgery, dimensions of one (1) mm or less are preferred, to access areas typically involved without damaging unrelated tissue.

Scanning mechanisms that allow time-dependent direction of light for diagnostic or therapeutic purposes have been used in endoscopic surgical instruments. These instruments typically use probes that provide imaging, treatment, or both, over an extended area of tissue without requiring motion of the endoscope relative to its surroundings. However, efforts to develop scanning endoprobes compatible with ophthalmic surgery have been slowed by the difficulty of providing the complex drive mechanisms in a compact form factor, at a low cost. This is particularly true for forward-directed scanning probes that may require counter rotating shafts with fixed or controlled relative speeds. For example, a rotation scanning probe is disclosed in U.S. Pat. No. 7,364,543 ('543 patent), incorporated herein by reference in its entirety. In patent '543 two different gear motors are used to counter-rotate tubes in a probe, unnecessarily complicating a probe design and implementation. Furthermore, inefficient use is made of the motor power since each motor is devoted to moving only one element.

Therefore, there is a need for simple and efficient rotational mechanisms for microsurgical probes.

SUMMARY

An endoprobe for microsurgical procedures according to embodiments disclosed herein may include a hand-piece including a motor, a cannula assembly coupled to the hand-piece, and a transmission system coupling the motor to the cannula assembly. Further the cannula assembly may include an outer tube able to rotate about a longitudinal axis and an inner tube concentric with the outer tube, able to rotate about the longitudinal axis. The outer tube and the inner tube each having a proximal end and a distal end; wherein the transmission system rotates the outer tube in a first direction and the inner tube in a second, opposing direction about the longitudinal axis; and further wherein a proximal space formed between the proximal ends of the outer tube and the inner tube includes at least a portion of the transmission system.

A cannula assembly for use in an endoprobe for microsurgical procedures according to some embodiments disclosed herein may include an outer tube able to rotate about a longitudinal axis and an inner tube concentric with at least a portion of the outer tube, able to rotate about the longitudinal axis. The outer and inner tubes may have a proximal end and a distal end with a proximal space formed between the proximal ends of the outer tube and the inner tube in a radial direction and a longitudinal direction. Further embodiments may include a transmission system placed in the proximal space and providing a counter-rotating motion to the outer tube and the inner tube.

An endoprobe for microsurgical procedures according to embodiments disclosed herein may include a hand-piece including a motor; a cannula assembly coupled to the hand-piece and a transmission system coupling the motor to the cannula assembly. The cannula assembly may include an outer tube able to rotate about a longitudinal axis and an inner tube concentric with the outer tube, able to rotate about the longitudinal axis. The outer and inner tube may each have a proximal end and a distal end; wherein the transmission system rotates and counter rotates the tubes; and wherein a counter-rotating motion is provided to the outer and inner tubes by the motor through the transmission system.

A method for scanning a light beam along a linear trajectory using a cannula assembly according to embodiments disclosed herein may include the step of providing a light beam through an axis of the cannula. A method according to embodiments disclosed herein may also include the step of using a transmission system in a proximal space of the cannula to provide a counter rotating motion to an outer tube and an inner tube; wherein each of the outer tube and inner tube is hollow and has an optical element in its distal end. Further, a method as above may include the step of controlling the relative rotating speeds of the outer tube and the inner tube using at least one gear in the transmission system.

These and other embodiments of the present invention will be described in further detail below with reference to the following drawings.

BRIEF DESCRIPTION OF THE DRAWINGS

FIG. 2A illustrates a partial cross-sectional view of a cannula assembly including two concentric drive tubes as shown in FIG. 1B and having a proximal space according to some embodiments.

FIG. 2B illustrates a partial cross-sectional view of a cannula assembly including two concentric drive tubes having a proximal space according to a further embodiment.

In the figures, elements having the same reference number have the same or similar functions.

DETAILED DESCRIPTION

Microsurgical procedures using endoscopic instruments may include a probe having a simple and cost-effective drive coupling mechanism. The probe may be a hand-held probe, for direct manipulation by specialized personnel. In some embodiments, the probe may be designed to be controlled by a robotic arm or a computer-controlled device. Probes have a proximal end close to the operation controller (be it a specialist or a device), and a distal end, close to or in contact with the tissue. Probes according to embodiments disclosed herein may have small dimensions, be easy to manipulate from a proximal end, and minimally invasive to the surrounding tissue. In the distal end, the probe ends with a tip, from where the probe performs certain action on a target tissue located in the vicinity of the tip. For example, the probe may deliver light from its tip, and receive light reflected or scattered from the tissue, coupled through the tip. The tip of the probe may include movable elements that enable the tip to perform its action.

Figures 1A, 1B:
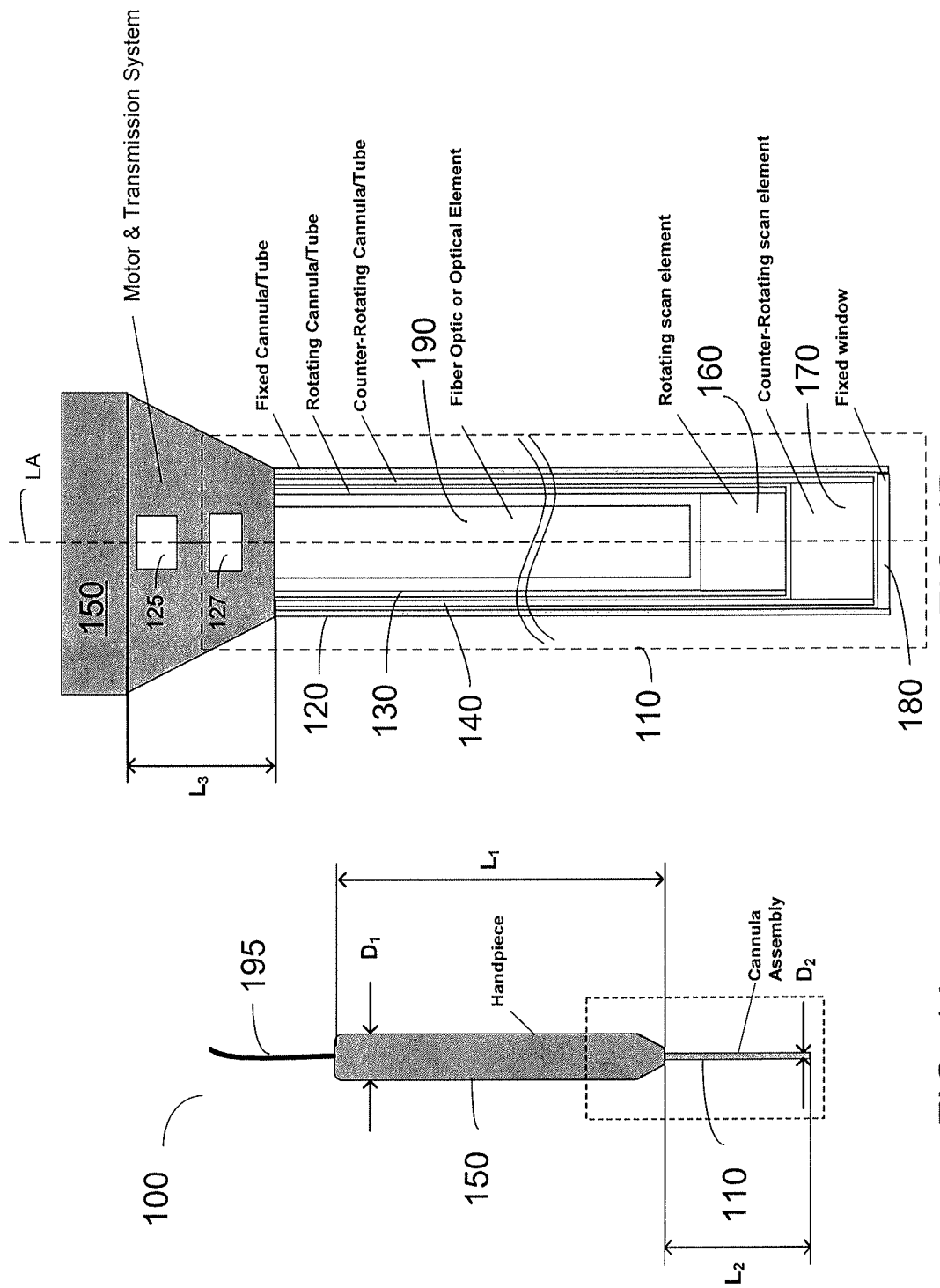
FIG. 1A illustrates a microsurgical endoprobe including an optical scanning element, a hand-piece, and a coupling cable according to some embodiments.
FIG. 1B illustrates a partial cross-sectional detail of the microsurgical endoprobe of FIG. 1A including a mechanical actuator, two concentric drive tubes, a rotating scan element and a counter-rotating scan element according to some embodiments.

FIG. 1A shows microsurgical endoprobe 100 including optical scanning element 110, hand-piece 150, and coupling cable 195, according to some embodiments. Scanning element 110 may also be referred to as a "cannula assembly" according to some embodiments. Element 110 includes the distal end of endoprobe 100 which may be elongated along the probe longitudinal axis and have a limited cross-section. For example, in some embodiments cannula assembly 110 may be about 0.5 mm in diameter ($D_2$) while hand-piece 150 may have a substantially cylindrical shape of several mm in diameter ($D_1$) such as 12-18 mm.

In some embodiments, assembly 110 may be in contact with tissue, including target tissue for the microsurgical procedure. Thus, assembly 110 may be coated with materials that prevent infection or contamination of the tissue. Furthermore, surgical procedures and protocols may establish hygienic standards for assembly 110. For example, it may be desirable that assembly 110 be disposed of after used once. In some situations, assembly 110 may be disposed of at least every time the procedure is performed on a different patient, or in a different part of the body.

Embodiments of endoprobe 10 and assembly 110 may comply with industry standards such as EN ISO 14971 (2007), "Medical Devices—Application of Risk Management to Medical Devices;" ISO/TS 20993 (2006), "Biological evaluation of medical devices—Guidance on a risk management process;" ISO 14001 (2004), "Environmental management systems—Requirements with guidance for use;" ISO 15752 (2009), "Ophthalmic instruments—endoilluminators—fundamental requirements and test methods for optical radiation safety;" and ISO 15004-2 (2007), "Ophthalmic instruments—fundamental requirements and test methods—Part 2: Light Hazard Protection." All above cited standard documents are herein incorporated by reference in their entirety.

Hand-piece 150 may be closer to the proximal end of the probe, and may have a larger cross section as compared to element 110. Element 150 may be adapted for manual operation of endoprobe 100, according to some embodiments. Element 150 may be adapted for robotic operation or for holding by an automated device, or a remotely operated device. While assembly 110 may be in contact with living tissue, element 150 may not be in direct contact with living tissue. Thus, even though element 150 may comply with hygienic standards, these may be somewhat relaxed as compared to those used for assembly 110. For example, element 150 may include parts and components of endoprobe 100 that may be used repeatedly before disposal.

Thus, some embodiments of endoprobe 100 as disclosed herein may include complex components in element 150, and less expensive, replaceable components may be included in assembly 110. Some embodiments may have a removable element 110 which is disposable, while hand-piece 150 may be used more than once. Hand-piece 150 may be sealed hermetically, in order to avoid contamination of the tissue with particulates or fumes emanating from internal elements in hand-piece 150. In some embodiments, cannula assembly 110 may be fixed to hand-piece 150 by an adhesive bonding. According to other embodiments, assembly 110 may be removable from hand-piece 150, to allow easy replacement of endoprobe 100 for repeated procedures. Some embodiments consistent with FIG. 1A may have a disposable element 150 and a disposable assembly 110.

Cable 195 may be included in some embodiments to couple endoprobe 100 to a remote console or controller device (not shown in FIG. 1A). Cable 195 may include power transmission elements, to transfer electrical or pneumatic power to a mechanical actuator, motor or motor inside element 150. Cable 195 may include transmission elements to carry optical information and power, such as a laser beam, from a remote console or controller to the tissue. An optical transmission element may also carry optical information from the tissue to a remote console or controller, for processing. For example, cable 195 may include at least one or more optical fibers to transmit light to and from the tissue. In some embodiments, one optical fiber may transmit light to the tissue, and another optical fiber may transmit light from the tissue. Further, some embodiments may transmit light to and from the tissue through one optical fiber.

According to some embodiments of endoprobe 100, cable 195 may be absent, and the probe may be wirelessly accessible. In such embodiments, a battery may be included in hand-piece 150 to provide electrical power to a motor and an optical light source. Further, in embodiments where hand-piece 150 is wireless, hand-piece 150 may include a transceiver device to send and receive data and instructions from the probe to a controller, and vice versa. In such embodiments, hand-piece 150 may also include a processor circuit having a memory circuit, to process data, control assembly 110, and control the transceiver device.

FIG. 1B shows a partial cross-sectional detail of microsurgical endoprobe 100 in FIG. 1A including motor 125, transmission system 127, and concentric tubes 130 and 140, according to some embodiments. Also shown in FIG. 1B are stationary cannula 120, rotating scan element 160, coupled to inner tube 130, counter-rotating scan element 170, coupled to tube 140, window 180 and optical transmission element 190. Transmission element 190 may include an optical fiber, or a plurality of optical fibers. As described above, element 190 may be coupled to cable 195 in the proximal end of assembly 110, and may transmit light into and from the tissue.

In some embodiments, motor 125 may be an electric motor. Some embodiments may include motors that use fluid flows to produce motion. For example, a pneumatic mechanism may be used as motor 125 in embodiments consistent with FIGS. 1A and 1B. Motor 125 may include an encoder to provide indication of the position of a rotating shaft within the motor at every point in time. The encoder may be coupled to the controller in a remote console through cable 195, or wirelessly, according to some embodiments.

In some embodiments such as illustrated in FIG. 1B, cannula assembly 110 may extend inside hand-piece 150. In the portion of assembly 110 inside element 150 assembly 110 may further include transmission system 127. System 127 may include a shaft and a set of gears to transfer the motion from motor 125 to moving components in assembly 110, as described below.

Further embodiments of motor 125 and transmission system 127 may be as disclosed in detail in U.S. patent application entitled "Pneumatically Driven Ophthalmic Scanning Endoprobe" by Mike Papac, Mike Yadlowsky, and John Huculak, Attorney Docket No. 3835/45463.38 filed on the same date as the present application and assigned to Alcon Laboratories, Inc. which is incorporated herein by reference in its entirety.

According to embodiments consistent with FIG. 1B, inner tube 130 may be aligned with its symmetry axis along the probe longitudinal axis (LA). Inner tube 130 may be a hollow tube of a material that provides rigidity to assembly 110 and support to element 160. Rotating scan element 160 may be attached to inner tube 130. Element 160 may be an optical element, according to some embodiments used in microsurgical procedures. For example, in forward-scan OCT techniques, element 160 may include a lens having one of its flat ends cut at a predetermined angle relative to the optical axis of the lens. In some embodiments, the lens may be arranged with its optical axis along the probe longitudinal axis, with its angled end on the distal side of the lens. In some embodiments the lens in element 160 may be a GRIN lens.

According to embodiments consistent with FIG. 1B, outer tube 140 may include a counter-rotating cannula tube coupled to counter-rotating scan element 170. Tube 140 may be a hollow tube of a material that provides rigidity to assembly 110 and support to element 170, aligned with its symmetry axis along the probe longitudinal axis (LA). Element 170 may be an optical element, according to some embodiments used in microsurgical procedures. For example, in forward-scan OCT techniques, element 170 may include a lens having one of its flat ends cut at a predetermined angle relative to the optical axis of the lens. In some embodiments, the GRIN lens may be arranged with its optical axis along the probe longitudinal axis, with its angled end on the proximal side of the lens. In some embodiments the lens in element 170 may be a GRIN lens.

In embodiments as described above, optical element 160 and optical element 170 may form a space or gap between them, along the probe longitudinal axis. The gap between elements 160 and 170 may be limited by two angled faces of a lens on either side, in some embodiments. As inner tube 130 and outer tube 140 are counter-rotated, a light beam passing through element 160 and element 170 may be deflected from the probe longitudinal axis at an angle θ given by the relative orientation of angled faces in elements 160 and 170. As elements 160 and 170 complete a full turn around the probe longitudinal axis, the light beam completes a full sweep substantially along a line in a plane containing the probe longitudinal axis. Some embodiments consistent with the above description may use probe 100 in an OCT-scanning procedure. OCT scanning procedures typically include an in-depth image obtained through an A-scan. A collection of A-scans along a line may form a 2-dimensional image in what is referred to as a B-scan. In such cases, the two counter-rotating optical elements 160 and 170 may provide a B-scan of the light beam used in OCT imaging.

A B-scan obtained as above may be substantially aligned along a radial direction perpendicular to the probe longitudinal axis (LA), on a projection plane perpendicular to and centered on the probe longitudinal axis. The specific orientation of the B-scan on the projection plane may be determined by the orientation of elements 160 and 170 at their maximum beam deflection position. In some embodiments, the position at which maximum beam deflection may be obtained is that in which the two angled faces of lenses included in elements 160 and 170 are opposing each other, forming a trapezoidal gap between them. The precise orientation of elements 160 and 170 relative to the projection plane thus gives the orientation of the radial B-scan on that plane. Thus, by adjusting the rotation speed of elements 160 and 170, the radial B-scan formed by the light beam on the projection plane may rotate around the probe longitudinal axis. As a result, in some embodiments the collection of A and B-scans may form a solid section of a cone with its axis along the probe longitudinal axis, having an aperture angle, θ. For example, the angle θ may be the maximum deflection of the light beam for any configuration of elements 160 and 170. In some embodiments this may occur when the two angled faces of lenses included in elements 160 and 170 are opposing each other.

Some embodiments using endoprobe 100 for OCT scans may provide a B-scan that is not a perfect line contained within a plane including the probe longitudinal axis. The B-scan provided by endoprobe 100 according to embodiments described above may have a shape resembling an elongated number '8,' substantially along a line in a plane containing the probe longitudinal axis. The details of the shape of the B-scan may be determined by parameters such as the size of the gap between elements 160 and 170. The shape of the resulting B-scan may also depend on the angle between the angled surfaces limiting the gap formed by elements 160 and 170. Also, the shape of the B-scan may be determined by the indexes of refraction of optical elements 160 and 170, and of the material inside the gap between elements 160 and 170.

The reference to inner tube 130 as "rotating" and outer tube 140 as "counter-rotating" is arbitrary and establishes the relative motion between tubes 130 and 140 about axis LA. In some embodiments, while tube 130 rotates 'clockwise,' tube 140 may rotate 'counter-clockwise.' The opposite configuration may occur, wherein tube 130 rotates 'counter-clockwise' and tube 140 rotates 'clockwise.'

According to embodiments consistent with FIG. 1B, window 180 may be provided. Furthermore, in embodiments of endoprobe 100 used for OCT scanning, window 180, attached to stationary cannula 120, may provide protection to optical components in assembly 110. Window 180 may prevent fluid from the target tissue contaminating lenses 160 and 170, or invading the gap between them. Thus, window 180 may ensure that lenses 160 and 170 are maintained in an environment surrounded by air, or any other fluid having a specified index of refraction.

Some embodiments consistent with FIG. 1B may include stationary cannula 120. Cannula 120 may provide a protective cover to assembly 110. Also, cannula 120 may prevent or reduce shear strain induced in the target tissue by viscoelastic forces acting upon the rotation of outer tube 140. The use of stationary cannula 120 is optional and may be determined by the type of target tissue where endoprobe 100 will be introduced.

The materials used to form cannula elements 120, 130, and 140 may be any of a variety of biocompatible materials. For example, some embodiments may include elements 120, 130 and 140 made of stainless steel, or plastic materials. Furthermore, some embodiments may have a portion or the entirety of elements 120, 130 and 140 coated with a protective layer. The coating material may be a gold layer, or some biocompatible polymer. In some embodiments the role of the coating layer may be to provide lubrication and friction relief to moving parts in assembly 110. For example, coating materials may reduce friction between the inner face of tube 140 and the outer face of tube 130. In some embodiments the role of the coating layer may be to provide protection to the tissue in direct contact with assembly 110.

Embodiments consistent with FIGS. 1A and 1B may include hand-piece 150 with a removable cannula assembly 110. Assembly 110 may be easily removable from hand-piece 150 by a snap-on mechanism, or a bayonet mechanism. Hand-piece 150 may include a bearing and a bushing coupled to the proximal end of tubes 120, 130 and 140 (not shown in FIG. 1B) to provide support and stability to assembly 110.

In embodiments such as shown in FIGS. 1A and 1B, it may be desirable that microsurgical endoprobe 100 have minimal cross sectional area. This may reduce the invasiveness of the surgical procedure on the target tissue, especially in areas adjacent to the areas of interest. In order to limit the cross sectional area of the cannula assembly in endoprobe 100, mechanical elements involved in moving parts of the probe need to be placed close together. To achieve this, embodiments such as depicted in FIGS. 2A and 2B may have an upper portion of outer tube 140 having a larger diameter. In addition to this, an upper portion of inner tube 130 may have a smaller diameter, as shown in FIG. 2B. This is described in detail as follows.

Table I illustrates a range of dimensions of different elements as labeled in FIGS. 1A and 1B according to some embodiments. In Table I, 'ID' refers to inner diameter, and 'OD' refers to outer diameter. Units in Table I are in microns ($1 \mu m = 10^{-6}$ m). The dimensions provided in Table I are nominal and can vary in different embodiments depending on the specific application. For example, some embodiments may vary endoprobe dimensions by about 50% from those in Table I. In embodiments of endoprobe 10 used for ophthalmic microsurgical procedures 'ODs' of less than approximately 1 to 1.5 mm are preferable.

TABLE I

| Element | OD max | OD min | ID max | ID min |
|---|---|---|---|---|
| 120 | 647.7 | 635 | 609.6 | 571.5 |
| 140 | 546.1 | 533.4 | 495.3 | 469.9 |
| 130 | 419.1 | 406.4 | 381 | 355.6 |
| 190 | 342.9 | 330.2 | 152.4 | 139.7 |

According to embodiments consistent with FIGS. 1A and 1B, the length $L_1$ of hand-piece 150 is 3-4 inches (approximately 7.5 cm to 10 cm). The length $L_2$ of cannula assembly 110 is 30 mm. According to some embodiments, cannula assembly 110 may have a portion extending inside hand-piece 150, adding to the length $L_2$ shown in FIG. 1A. The length $L_3$ of the tapered portion of hand-piece 150 may depend on ergonomic and cosmetic considerations. In some embodiments length $L_3$ may be approximately 6 mm.

FIG. 2A shows a partial cross-sectional view of assembly 200-1 including concentric drive tubes 130-1 and 140 as in FIG. 1B, according to some embodiments. Tube 130-1 may be a straight cylindrical section, concentric with tube 140 and with a smaller diameter than tube 140. Tube 140 may include two sections: 140a in the proximal end and 140b in the distal end. Each of sections 140a and 140b may be concentric with tube 130-1, having a larger diameter than tube 130-1. In some embodiments consistent with FIG. 2A, section 140a may have a larger diameter than section 140b. This configuration provides additional space 220 in the proximal area of tube 140 so that mechanical components may be included in assembly 200-1. Some embodiments may include gears, washers, gaskets and shafts in proximal space 220.

FIG. 2B shows a partial cross-sectional view of assembly 200-2 including concentric drive tubes 130-2 and 140 according to some embodiments. While tube 140 in FIG. 2B may be as described in relation to FIG. 2A, tube 130-2 may include proximal portion 130a and distal portion 130b. In some embodiments consistent with FIG. 2B, portion 130a may have a smaller diameter than portion 130b. Thus, proximal space 220 in assembly 200-2 may be further increased in relation to embodiments consistent with assembly 200-1.

According to embodiments consistent with FIGS. 2A and 2B, linkage portion 210 may be provided to couple section 140a and 140b in tube 140. Linkage 210 may be such that no relative motion may be allowed between sections 140a and 140b. In some embodiments, linkage 210 may be made of a rubber material or some other resilient material that allows certain amount of motion between portions 140a and 140b. This may provide a degree of flexibility to assembly 200-1 and 200-2, which may be desirable to reduce strain induced in the target tissue by endoprobe 100. In some embodiments it may be desirable to provide a water sealing material in linkage 210, so that no humidity or fluids from the tissue may contaminate space 220 and the space between tubes 130 and 140. Having linkage 210 to hermetically seal space 220 and the inner space between tubes 130 and 140 may also protect the target tissue from contamination from particulates or materials from inside assembly 200-1 or 200-2. Linkage portion 210 may also be used to couple sections 130a and 130b in tube 130-2, according to embodiments consistent with FIG. 2B.

Figure 3:
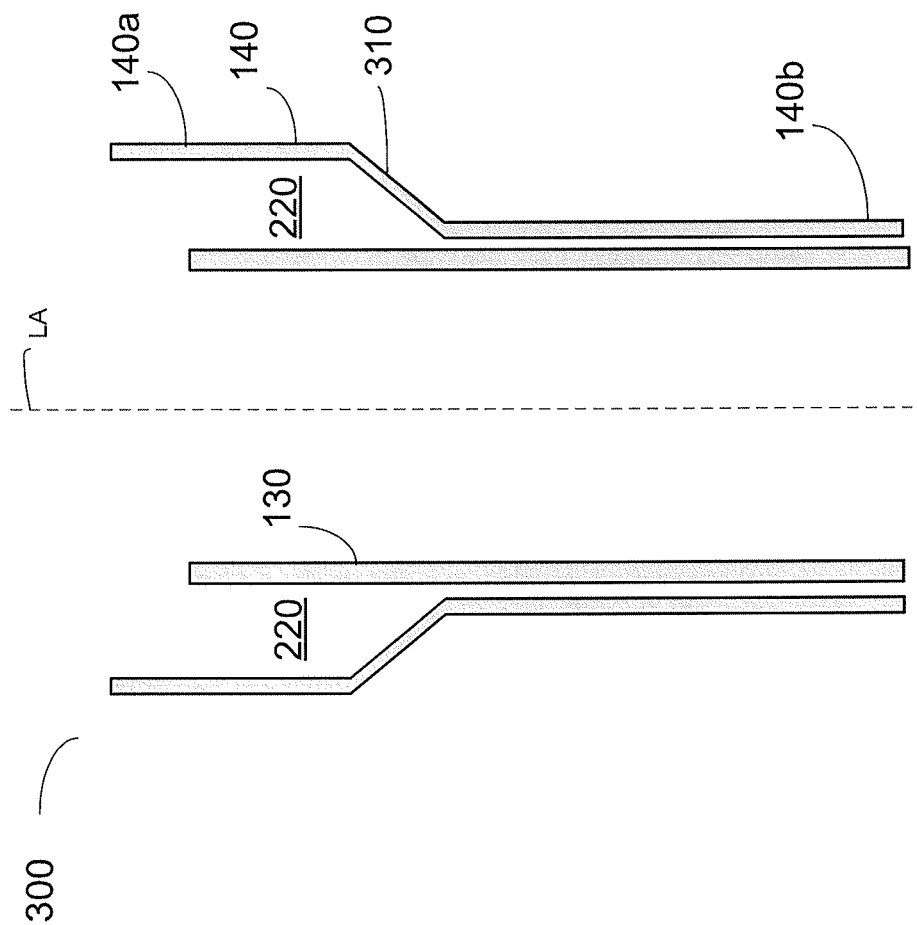
FIG. 3 illustrates a partial cross-sectional view of a cannula assembly including two concentric drive tubes having a proximal space according to still a further embodiment.

FIG. 3 shows a partial cross-sectional view of assembly 300 including concentric drive tubes 130 and 140, according to some embodiments. As in assemblies 200-1 and 200-2, outer tube 140 may have proximal portion 140a with a larger diameter than distal portion 140b. Further, embodiments consistent with assembly 300 may include flared portion 310 coupling proximal portion 140a and distal portion 140b. While portions 140a, 310 and 140b may be coupled together as shown in FIG. 3, they may be made of different materials and have different physical properties. In some embodiments, portions 140a, 310, and 140b may be made of the same material and have similar physical properties. Embodiments such as depicted in FIG. 3 may achieve an assembly 300 with reduced cross sectional area in the distal end and a wide proximal space 220. This may improve the clearance between tubes 130 and 140 in assembly 300. While this may result in less precise tolerances, it may also reduce significantly the cost of assembly 300.

Figure 4:
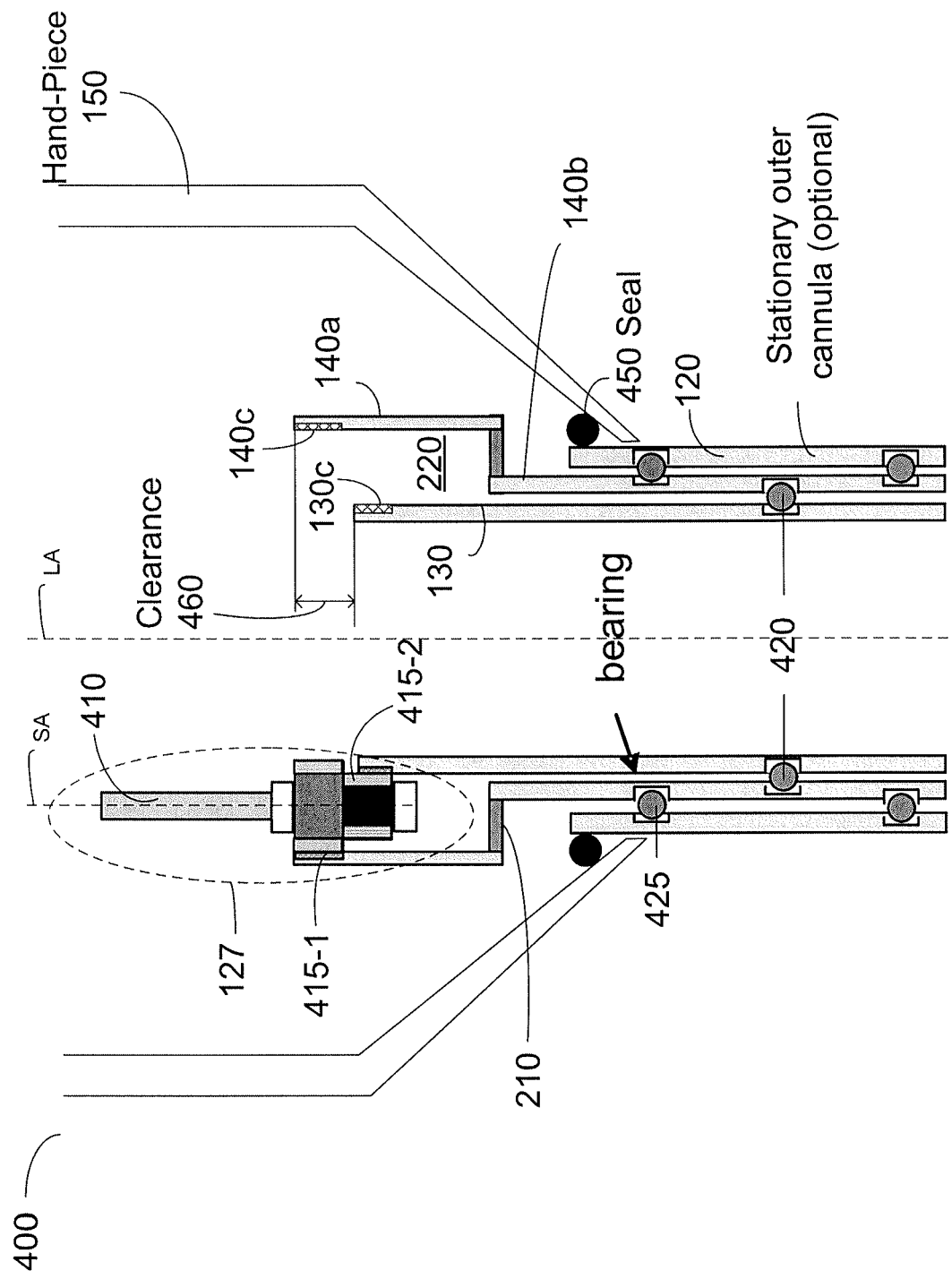
FIG. 4 illustrates a partial cross-sectional view of a cannula assembly including a mechanical actuator in a proximal space further including a gear drive according to some embodiments.

FIG. 4 shows a partial cross-sectional view of assembly 400 including transmission system 127 further including shaft 410 and gears 415-1 and 415-2, according to some embodiments. Embodiments consistent with FIG. 4 may also include bearings 420 coupling inner tube 130 to outer tube 140, and bearings 425 coupling outer tube 140 to stationary outer cannula 120. Stationary cannula 120 may be attached to assembly 400 and maintain positioning of the rotating tubes relative to the drive gears. Stationary cannula 120 has been described in detail in relation to FIG. 1. Linkage portion 210 in tube 140, together with proximal portion 140a and distal portion 140b may be as described in detail with relation to FIG. 2 above. Bearings 420 and 425 provide frictional relief for the inter-space between tube 130 and 140, and between stationary cannula 120 and tube 140, respectively. The use of bearings 420 and 425 may depend on the length of assembly 400 and the diameter of tubes 130 and 140. For example, the aspect ratio of the diameter of outer tube 140 to the length of assembly 400 may determine the use of bearings 420 and 425, and their interspacing along the probe longitudinal axis.

As illustrated in FIG. 4, hand-piece 150 may include a portion of cannula assembly 110 in its distal end. Furthermore, hand-piece 150 may include a resilient material forming seal 450 to avoid any contamination or exchange of material between the interior of hand-piece 150 and the tissue being treated. Seal 450 may be made of a resilient material such as rubber, or a biocompatible polymer. Furthermore, in some embodiments seal 450 may be made of a metal such as copper or aluminum.

According to embodiments consistent with FIG. 4, system 127 may be included in proximal space 220. System 127 may be a transmission mechanism coupling the action of motor 125 (not shown in FIG. 4) to inner tube 130 and outer tube 140. In order to provide a rotational motion to tube 130 and tube 140, transmission system 127 may include shaft 410 and gears 415-1 and 415-2. Shaft 410 is coupled to motor 125, which provides shaft 410 with rotation about its axis. According to FIG. 4, shaft 410 may be parallel to the probe longitudinal axis. Some embodiments may have shaft 410 aligned in a direction not parallel to the probe longitudinal axis. For example, in some embodiments consistent with the concept of FIG. 4 shaft 410 may be in a plane perpendicular to the probe longitudinal axis. Furthermore, according to FIG. 4, shaft 410 may provide motion by rotating about its axis. Some embodiments may have shaft 410 providing motion to tubes 130 and 140 by moving linearly and periodically up and down, about its axis.

According to FIG. 4, gear 415-2 may be coupled to inner tube in portion 130c, and gear 415-1 coupled to outer tube 140 in portion 140c. Portion 130c may be a section in the outer side of the proximal end in tube 130. Portion 140c may be a section in the inner side of the proximal end in tube 140. Portion 140c may be included in portion 140a of outer tube 140. To couple tubes 130 and 140 to gears 415-1 and 415-2, portions 130c and 140c may include gear teeth cut in or attached to tubes 130 and 140, respectively. The gear teeth in portions 130c and 140c may match corresponding teeth on two separate gears 415 in transmission system 127. Some embodiments may use a friction gear such as a polymer disk in place of a toothed gear. Embodiments consistent with FIG. 4 may have gears 415-1 and 415-2 formed of a variety of materials, such as stainless steel, plastic, or hardened rubber. Other metals such as copper or aluminum may also be used to form gears 415-1 and 415-2.

FIG. 4 also illustrates clearance space 460 in the longitudinal direction between the proximal ends of outer tube 140 and inner tube 130. Clearance space 460 provides space to portions of transmission system 127 that may not contact inner tube 130. For example, in embodiments consistent with FIG. 4, clearance space 460 provides space to gear 415-1, having a diameter larger than that of gear 415-2. Thus, gear 415-1 may rotate tube 140 without contacting inner tube 130 or obstructing the rotation of tube 130.

Gears 415-1 and 415-2 in transmission system 127 may be adapted so as to rotate inner tube 130 in one direction and outer tube 140 in an opposite direction using the same drive shaft 410. This may allow tubes 130 and 140 to counter-rotate synchronously. In some embodiments, such as depicted in FIG. 4, gears 415-1 and 415-2 may be attached to shaft 410 in a way that the two gears may rotate in the same direction. Gear 415-1 may be coupled to the inner side of tube 140 through portion 140c. Gear 415-2 may be coupled to the outer side of tube 130 through portion 130c. Thus, a counter-rotating effect between tubes 130 and 140 may be obtained as shaft 410 rotates in a given direction. By using gears 415-1 and 415-2 having an appropriate radius relation, the rotational speed of tube 130 may be adjusted in relation to the counter-rotational speed of tube 140. For example, in embodiments consistent with FIG. 4 gear 415-2 coupling shaft 410 to inner tube 130 may have a smaller radius than gear 415-1 coupling shaft 410 to outer tube 140. This may result in inner tube 130 rotating at the same speed and in the opposite direction relative to tube 140. Different arrangements for the relative speeds of tubes 130 and 140 may be provided by gears 415-1 and 415-2 in transmission system 127.

Some embodiments may use gears 415-1 and 415-2 having radii to provide different rotational speeds in tubes 130 and 140. For example, some embodiments may be such that while inner tube 130 completes one turn, outer tube completes 10 or 100 counter turns. In general, while inner tube 130 completes 'P' turns, outer tube 140 may complete 'Q' turns, where 'P' and 'Q' may be any two integer numbers. Furthermore, the ratio between the frequency of rotation in tube 140 and the rotation in tube 130 may be an irrational number. In some embodiments, the frequency of rotation of one of tubes (130 or 140) may be a harmonic of the frequency of rotation of the other tube (140 or 130).

Furthermore, in order to minimize abrasion to the tissue in direct contact with cannula assembly 110, some embodiments of transmission system 127 may provide a 'spooling' motion. A 'spooling' motion is such that tubes 130 and 140 rotate in one direction for one cycle, and switch to rotate in the opposite direction in the next cycle. Thus, while the scanning effect is still a linear trajectory, the tissue surrounding assembly 110 is subjected to reduced shear.

According to some embodiments consistent with FIG. 4, motor 125 (cf. FIG. 1) may provide a rotation speed to shaft 410 varying form 1 Hz (one turn per second) up to 1 kHz (one thousand turns per second) or more. Shaft 410 rotates around shaft axis (SA) that is substantially parallel to axis LA and radially offset by a distance greater than one half the OD of tube 130. In a further aspect, axis SA is offset from axis LA by a distance greater than one half the OD of portion 140b in tube 140, but less than one half the OD of tube 120.

The relative sizes of gears 415-1 and 415-2, and of inner tube 130 and outer tube 140, determines the rotating speed of tubes 140 and 130. In some embodiments, tubes 130 and 140 may rotate each with a speed of a few RPM (revolutions per minute) to tens of RPM or even higher, such as 100 RPM or more. While the relative rotational speed of tubes 130 and 140 is within a few tens of RPM, no heat dissipation may induce a thermal gradient sufficient to affect the surrounding tissue. Furthermore, under conditions of a few tens of RPM of relative rotational speed, heat dissipation through a lubricant coating layer may be sufficient to avoid thermal breakdown of cannula assembly 110. Such lubricant coating layer may be a polymer coating as discussed above, or Teflon.

In some embodiments, the rotating and counter rotating speeds of tubes 130 and 140 may be substantially higher, such as 8200 RPM or more. For example, in embodiments where endoprobe 10 is used for OCT scanning, a fast rotation speed may be desired. In such cases, the maximum speed of rotation of tubes 130 and 140 may be limited by the detector acquisition speed in the OCT scanner. Furthermore, some embodiments using a 'spooling' motion may use a rotating and counter-rotating speed for tubes 130 and 140 that is double the speed for a continuous motion. For example, in embodiments of endoprobe 10 for OCT scanning, a configuration using a 'spooling' motion may rotate at twice the speed of a configuration using a continuous motion to complete the same B-scan. A high rotational speed may be desirable in OCT-scanning embodiments in order to produce 3D volume imaging.

Figure 5:
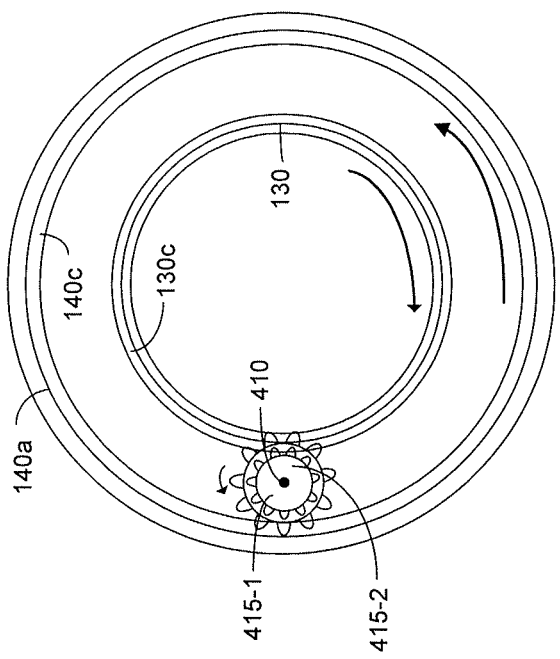
FIG. 5 illustrates a cannula assembly as in FIG. 4 from a top-to-bottom view, according to some embodiments.

FIG. 5 illustrates cannula assembly 110 as in FIG. 4 from a top-to-bottom view, according to some embodiments. According to FIG. 5, shaft 410 may rotate counter-clockwise, and gear 415-1 provides a counter-clockwise rotating motion to outer tube 140 by engaging its teeth to portion 140c. In turn, gear 415-2 provides a clockwise rotating motion to inner tube 130, by engaging its teeth to portion 130c. Other elements from FIG. 4 are not shown in FIG. 5 for clarity.

A probe according to embodiments disclosed herein may provide a simple, efficient mechanism to generate precisely controlled counter rotational motion in two concentric tubes. Such a probe may be used as an OCT imaging probe, or a multi-spot laser probe. While probes may have 3-dimensional layouts, they may be highly constrained in cross-section, and elongated in a certain direction. Furthermore, in some embodiments the probes may be axially symmetric, at least in a portion of the probe which may include the distal end.

In OCT imaging techniques, a light beam having a coherence length may be directed to a certain spot in the target tissue by using a probe. The coherence length provides a resolution depth, which when varied at the distal end of the probe may be de-convolved to produce an in-depth image of the illuminated portion of the tissue (A-scan). A 2-dimensional tissue image may be obtained through a B-scan. In some embodiments, B-scans are straight lines along a cross-section of the tissue. Furthermore, by performing repeated B-scans along different lines in the tissue, a 3D rendition of the tissue may be provided. In some embodiments, the B-scans may be a set of lines having the same length and arranged in a radius from a common crossing point. Thus, the plurality of B-scans provides an image of a circular area in the tissue, having a depth.

According to some embodiments of endoprobe 10 used for OCT-imaging, a plurality of A-scans may be completed for each B-scan step. For example, 512 A-scans may be used to complete one B-scan. Some embodiments may use a lower number of A-scan per B-scan cycle, thus allowing the B-scan procedure to take place at a faster rate. In such cases, the rotating and counter-rotating speeds of tubes 130 and 140 may be further increased.

To obtain a complex set of scan lines, including B-scan lines arranged in pre-selected patterns, inner tube 130 and outer tube 140 in probe 10 may be used. Tubes 130 and 140 may include delicate optical components moved to steer a light beam along a desired direction. Precise control of this motion is important for the efficacy of OCT procedures. In particular, repeatability of the motion may be required so that A-scans may be aligned along B-scan lines to conform a continuous image. In some embodiments, the motion of movable parts in the probe may be a periodic cycle having a closed trajectory. For example, a trajectory may be circular, centered on the probe longitudinal axis. The probe longitudinal axis may be the optical axis of an optical system.

A substantially one dimensional probe having a symmetry axis according to some embodiments disclosed herein may provide a radial-oriented B-scan about the probe's longitudinal axis. To achieve this, counter-rotating tubes 130 and 140 may be used, synchronized accordingly by transmission system 127. For example, counter-rotating tubes 130 and 140 may provide optical scanning of a beam along a radial direction in a plane perpendicular to and centered on the probe longitudinal axis. Such an arrangement may use optical elements as described in detail in the paper by Wu et al. incorporated herein by reference in its entirety (J. Wu, M. Conry, C. Gu, F. Wang, Z. Yaqoob, and C. Yang; "'Paired-angle-rotation scanning optical coherence tomography forward-imaging probe" Optics Letters, 31(9) 1265 (2006)). Some embodiments may include a synchronization mechanism in transmission system 127 such that the relative phase and speed of tubes 130 and 140 may be regulated as desired. Thus, tubes 130 and 140 may provide linear radial scanning along a plane including the probe longitudinal axis. Furthermore, by adjusting the relative angular speeds and phases of tubes 130 and 140, the plane of the radial scan may be rotated about the probe longitudinal axis. Some embodiments as described above may be such that the radial scan is not perfectly linear. That is, the optical beam may not move in a perfect line contained within a plane including the probe longitudinal axis. In some embodiments the motion may be substantially close to the plane, on an elongated trajectory substantially close to a line in the plane. In some embodiments, the trajectory of the optical beam may form an elongated '8' figure on a plane perpendicular to and centered on the probe longitudinal axis.

In some embodiments, OCT techniques use forward-directed scan procedures. In this case, optical illumination takes place in the forward direction of the probe longitudinal axis. In forward-directed scans, the target tissue may be ahead of the probe in a plane perpendicular to the probe longitudinal axis. Thus, light traveling from the tip of the probe to the tissue, and back from the tissue into the probe may travel in a direction substantially parallel to the probe longitudinal axis. In some embodiments using forward-directed scans, the target tissue may be approximately perpendicular to the probe longitudinal axis, but not exactly. Furthermore, in some embodiments light traveling to and from the target tissue from and into the probe may not be parallel to the probe longitudinal axis, but form a symmetric pattern about the probe longitudinal axis. For example, light illuminating the target tissue in a forward-directed scan may form a solid cone or a portion thereof about the probe longitudinal axis. Likewise, light collected by endoprobe 10 in a forward-directed scan may come from target tissue in a 3D region including a portion of a cone section around the probe longitudinal axis.

In some embodiments, an OCT technique may use side imaging. For example, in side imaging the target tissue may be parallel to a plane containing the probe longitudinal axis. In a situation like this, it may be desirable to move the illumination spot in a circular trajectory around the probe longitudinal axis, to create a closed-loop image of the target tissue. Such a situation may arise in microsurgery involving endovascular procedures. For example, in coronary angiography the interior wall of the coronary artery may be fully scanned in cylindrical sections along the arterial lumen using embodiments described herein.

Some embodiments may use endoprobe 10 as provided herein for delivery of laser light intended for therapeutic purposes. For example, in photodynamic procedures a laser light may be scanned to activate a chemical agent present in a drug previously delivered to the target tissue. In some embodiments, laser light may be used to selectively oblate or remove tissue or residual materials from the target areas. In embodiments such as previously described, precise control of the light being delivered is provided by movable components in the distal end of the probe.

Note that the conversion of rotational motion into linear motion according to some embodiments disclosed herein provides a smooth mechanism to perform a linear motion. While rotational motion may be provided continuously, a cyclic linear motion may require stoppage and acceleration of a mechanical element, if tried directly. Stoppage and acceleration of a mechanical element subject to friction may not be desirable.

Embodiments of the invention described above are exemplary only. One skilled in the art may recognize various alternative embodiments from those specifically disclosed. Those alternative embodiments are also intended to be within the scope of this disclosure. As such, the invention is limited only by the following claims.

What is claimed is:

1. An endoprobe for microsurgical procedures comprising:
a hand-piece comprising a motor;
a cannula assembly coupled to the hand-piece;
a transmission system coupling the motor to the cannula assembly;
the cannula assembly comprising:
an outer tube able to rotate about a longitudinal axis;
an inner tube concentric with the outer tube, able to rotate about the longitudinal axis;
the outer tube and the inner tube each having a proximal end and a distal end; wherein
the transmission system rotates the outer tube in a first direction and the inner tube in a second, opposing direction about the longitudinal axis;
a proximal space formed between the proximal ends of the outer tube and the inner tube comprises at least a portion of the transmission system;
the transmission system extending into the proximal space and being located between the inner tube and the outer tube in a radial direction; and
the transmission system comprises at least one gear-assembly which couples the motor to the inner side of the outer tube and to the outer side of the inner tube.

2. The endoprobe of claim 1 further wherein the proximal end of the inner tube provides a clearance space in the longitudinal direction for the transmission system.

3. The endoprobe of claim 1 further comprising a stationary tube concentric and exterior to the outer tube, having a proximal end and a distal end.

4. The endoprobe of claim 1 wherein the microsurgical procedures involve the use of light, the endoprobe comprising:
optical components attached to the outer tube and the inner tube; and wherein
the counter rotating motion of the outer tube and the inner tube provides a scanning of a light beam; further wherein the outer tube and the inner tube are hollow.

5. The endoprobe of claim 4 wherein the optical components comprise at least one lens attached to each of the inner tube and outer tubes.

6. The endoprobe of claim 5 wherein the at least two lenses form a gap having the sides of the lenses facing the gap cut at an angle relative to the axis of each lens.

7. The endoprobe of claim 6 wherein the at least one lens comprises at least one GRIN lens.

8. The endoprobe of claim 4 wherein the optical components comprise at least one prism.

9. The endoprobe of claim 4 wherein the optical components comprise at least one diffractive element.

10. The endoprobe of claim 1 wherein the proximal end of the outer tube has a larger diameter than the distal end, to provide for the proximal space.

11. The endoprobe of claim 10 wherein the proximal end of the inner tube has a smaller diameter than the distal end to increase the proximal space.

12. The endoprobe of claim 1 comprising bearings between the outer tube and the inner tube; and
the bearings are placed at regular spaces along the space between the outer tube and the inner tube.

13. The endoprobe of claim 1 comprising a stationary cannula outside the outer tube.

14. The endoprobe of claim 13 comprising bearings placed between the stationary cannula and the outer tube.

15. A cannula assembly for use in an endoprobe for microsurgical procedures, comprising:
an outer tube able to rotate about a longitudinal axis;
an inner tube concentric with the outer tube, able to rotate about the longitudinal axis;
the outer and inner tubes having a proximal end and a distal end;
a proximal space formed between the proximal ends of the outer tube and the inner tube, the proximal space extending in a radial direction and a longitudinal direction;
a transmission system placed in the proximal space and providing a rotating motion to the outer tube and a counter-rotating motion to the inner tube,
the transmission system extending into the proximal space and being located between the inner tube and the outer tube in a radial direction;
wherein the transmission system comprises at least one gear-assembly which couples the motor to the inner side of the outer tube and to the outer side of the inner tube.

16. The assembly of claim 15, further comprising a detachable portion to a hand-held piece; the hand-held piece comprising a motor coupled to the transmission system.

17. The assembly of claim 15 further comprising a stationary cannula concentric and exterior to the outer tube, having a proximal end and a distal end.

* * * * *